US012576075B2

(12) United States Patent
Makhov et al.

(10) Patent No.: US 12,576,075 B2
(45) Date of Patent: Mar. 17, 2026

(54) COMBINATION THERAPIES FOR TREATING CANCER

(71) Applicant: Institute For Cancer Research, Philadelphia, PA (US)

(72) Inventors: Petr Makhov, Philadelphia, PA (US); Vladimir Kolenko, Philadelphia, PA (US)

(73) Assignee: INSTITUTE FOR CANCER RESEARCH, Philadelphia, PA (US)

( * ) Notice: Subject to any disclaimer, the term of this patent is extended or adjusted under 35 U.S.C. 154(b) by 1132 days.

(21) Appl. No.: 17/288,982

(22) PCT Filed: Oct. 30, 2019

(86) PCT No.: PCT/US2019/058791
§ 371 (c)(1),
(2) Date: Apr. 27, 2021

(87) PCT Pub. No.: WO2020/092517
PCT Pub. Date: May 7, 2020

(65) Prior Publication Data
US 2021/0379047 A1 Dec. 9, 2021

Related U.S. Application Data

(60) Provisional application No. 62/752,417, filed on Oct. 30, 2018.

(51) Int. Cl.
| | |
|---|---|
| *A61K 31/4545* | (2006.01) |
| *A61K 9/00* | (2006.01) |
| *A61K 31/404* | (2006.01) |
| *A61K 31/4709* | (2006.01) |
| *A61K 45/06* | (2006.01) |
| *A61P 35/04* | (2006.01) |

(52) U.S. Cl.
CPC ........ *A61K 31/4545* (2013.01); *A61K 9/0053* (2013.01); *A61K 31/404* (2013.01); *A61K 31/4709* (2013.01); *A61K 45/06* (2013.01); *A61P 35/04* (2018.01)

(58) Field of Classification Search
CPC .............. A61K 31/4545; A61K 9/0053; A61K 31/404; A61K 31/4709; A61K 45/06; A61K 9/0014; A61K 9/0024; A61K 9/0095; A61K 9/06; A61K 9/08; A61K 9/10; A61K 9/107; A61K 9/12; A61K 9/122; A61K 9/2004; A61K 9/4841; A61K 9/7023; A61K 9/0019; A61K 31/44; A61K 31/4439; A61K 31/517; A61P 35/04
See application file for complete search history.

(56) References Cited

U.S. PATENT DOCUMENTS

| | | |
|---|---|---|
| 2006/0281755 A1 | 12/2006 | Baumann et al. |
| 2013/0130999 A1 | 5/2013 | Vener et al. |
| 2013/0202709 A1 | 8/2013 | Desai et al. |
| 2016/0339025 A1 | 11/2016 | Ibrahim et al. |
| 2017/0088613 A1 | 3/2017 | Grogan et al. |
| 2021/0169801 A1 | 6/2021 | Na et al. |
| 2021/0214335 A1 | 7/2021 | Sheng et al. |
| 2021/0379047 A1 | 12/2021 | Makhov et al. |
| 2022/0002396 A1 | 1/2022 | Gualberto |

FOREIGN PATENT DOCUMENTS

| | | | |
|---|---|---|---|
| WO | 2014160729 | 10/2014 | |
| WO | WO 2014/160729 A1 * | 10/2014 | ............... A61K 9/20 |

OTHER PUBLICATIONS

Heike Niessner et al. The Farnesyl Transferase Inhibitor Lonafarnib Inhibits mTOR Signaling and Enforces Sorafenib-Induced Apoptosis in Melanoma Cells, Journal of Investigative Dermatology, 2011, 131(2):468-479 (Year: 2011).*
Christophe Le Tourneau, Eric Raymond & Sandrine Faivre; Sunitinib: a novel tyrosine kinase inhibitor. A brief review of its therapeutic potential in the treatment of renal carcinoma and gastrointestinal stromal tumors (GIST), Therapeutics and Clinical Risk Management, 2007, 3(2): 341-348 (Year: 2007).*
Patrick Schöffski et al., Crizotinib achieves long-lasting disease control in advanced papillary renal-cell carcinoma type 1 patients with MET mutations or amplification. European Journal of Cancer, 2017, 87:147-163 (Year: 2017).*
Hong DS et al., Inhibition of the Ras/Raf/MEK/ERK and RET kinase pathways with the combination of the multikinase inhibitor sorafenib and the farnesyltransferase inhibitor tipifarnib in medullary and differentiated thyroid malignancies. J Clin Endocrinol Metab., 2011, 96(4):997-1005 (Year: 2011).*
Kim A, Balis FM, Widemann BC. Sorafenib and sunitinib. Oncologist, 2009, 14(8):800-805 (Year: 2009).*
Vogus, Douglas R., et al. Bioengineering & Translational Medicine, 2018, 3:49-57 (Year: 2018).*
Niessner et al., "The Farnesyl Transferase Inhibitor Lonafarnib Inhibits mTOR Signaling and Enforces Sorafenib-Induced Apoptosis in Melanoma Cells", Journal of Investigative Dermatology, 2015, 131, pp. 468-479.
Jazieh et al., "A phase I study of the farnesyltransferase inhibitor Tipifarnib in combination with the epidermal growth factor tyrosine kinase inhibitor erlotinib in patients with advanced solid tumors", Investigational New Drugs, 2018, 37 (2), pp. 307-314.
Brown et al., "Novel approaches in the treatment of thyroid cancer", Update on Cancer Therapeutics, 2008, 3(1), pp. 1-11.
Hong et al., "Phase I Trial of a Combination of the Multikinase Inhibitor Sorafenib and the Farnesyltransferase Inhibitor Tipifarnib in Advanced Malignancies", Clinical Cancer Research, 2009, 15(22), pp. 7061-7068.

(Continued)

*Primary Examiner* — Joseph K McKane
*Assistant Examiner* — David M Shim
(74) *Attorney, Agent, or Firm* — DUANE MORRIS LLP

(57) ABSTRACT

Pharmaceutical compositions comprising a tyrosine kinase inhibitor and a farnesyltransferase inhibitor, or pharmaceutically acceptable salts thereof, and a pharmaceutically acceptable carrier, as well as methods for preventing or treating cancer by administering the same are disclosed herein.

5 Claims, 5 Drawing Sheets

(56) References Cited

OTHER PUBLICATIONS

Narayanan et al., "Current Standards in Treatment of Radioiodine Refractory Thyroid Cancer", Current Treatment Options in Oncology, 2016, 17(6), pp. 1-22.

Haluska et al., "Farnesyl transferase inhibitors as anticancer agents", European Journal of Cancer, 2002, 38(13), pp. 1685-1700.

Tsai, Chun-Ming et al., "Antagonism between Gefitinib and Cisplatin in Non-small Cell Lung Cancer Cells", Journal of Thoracic Oncology, vol. 6, No. 3, Mar. 2011, pp. 559-568.

* cited by examiner

COMBINATION THERAPIES FOR TREATING CANCER

REFERENCE TO GOVERNMENT GRANTS

This invention was made with government support under CA216173, and CA167671 awarded by the National Institutes of Health. The government has certain rights in the invention.

FIELD

The present disclosure is directed, in part, to combinations of farnesyltransferase inhibitors and tyrosine kinase inhibitors, or pharmaceutically acceptable salts thereof, compositions comprising the same, kits comprising the same, and methods of preventing or treating cancer by administering the same.

BACKGROUND

Current targeted molecular strategies employing tyrosine kinase inhibitors (TIs) have resulted in significant gains in overall survival in certain cancer subtypes. Despite the therapeutic progress, however, complete and robust responses have been noted in only a few cases. Furthermore, in some cancer subtypes patients are primarily refractory to treatment with TKIs. Farnesyltransferase (FTase)-dependent proteins regulate endosomal/lysosomal formation.

SUMMARY

The present disclosure provides pharmaceutical compositions comprising: a tyrosine kinase inhibitor chosen from sunitinib, axitinib, sorafenib, and erlotinib, or a pharmaceutically acceptable salt thereof; a farnesyltransferase inhibitor chosen from lonafarnib and tipifarnib, or a pharmaceutically acceptable salt thereof; and a pharmaceutically acceptable carrier.

The present disclosure also provides methods of treating cancer in a subject in need thereof comprising administering to the subject a tyrosine kinase inhibitor chosen from sunitinib, axitinib, sorafenib, and erlotinib, or a pharmaceutically acceptable salt thereof; and administering to the subject a farnesyltransferase inhibitor chosen from lonafarnib and tipifarnib, or a pharmaceutically acceptable salt thereof. In some embodiments, the tyrosine kinase inhibitor and the farnesyltransferase inhibitor are present in a single pharmaceutical composition.

The present disclosure also provides combinations of a tyrosine kinase inhibitor chosen from sunitinib, axitinib, sorafenib, and erlotinib, or a pharmaceutically acceptable salt thereof, and a farnesyltransferase inhibitor chosen from lonafarnib and tipifarnib, or a pharmaceutically acceptable salt thereof for use in the manufacture of a medicament for treating cancer.

The present disclosure also provides uses of a pharmaceutical composition comprising a tyrosine kinase inhibitor chosen from sunitinib, axitinib, sorafenib, and erlotinib, or a pharmaceutically acceptable salt thereof, and a farnesyltransferase inhibitor chosen from lonafarnib and tipifarnib, or a pharmaceutically acceptable salt thereof, for treating cancer.

DESCRIPTION OF EMBODIMENTS

Figure 1:
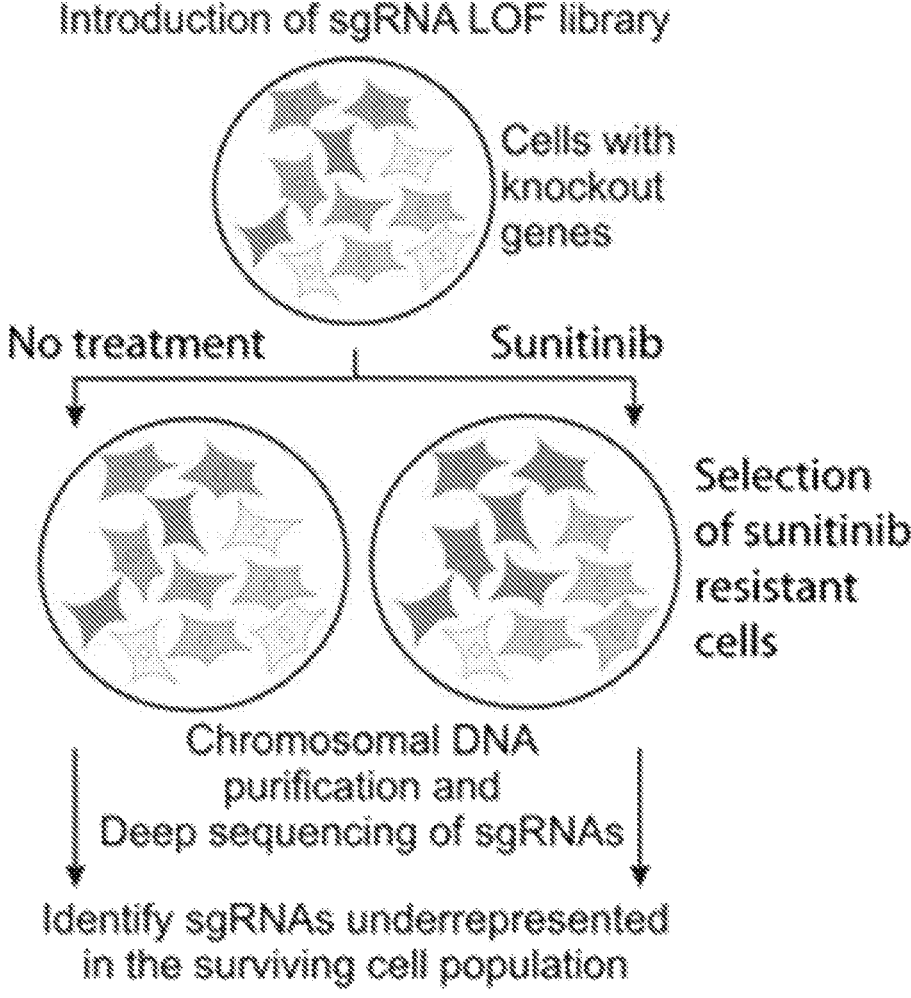
FIG. 1 shows a representative selection strategy to screen Loss of Function (LOF) libraries to identify genes involved in sunitinib resistance in renal cell carcinoma (RCC) tumors.

Various publications, including patents, published applications, technical articles and scholarly articles are cited throughout the specification. Each of these cited publications is incorporated by reference herein, in its entirety and for all purposes.

Unless defined otherwise, all technical and scientific terms have the same meaning as is commonly understood by one of ordinary skill in the art to which the disclosed embodiments belong.

As used herein, the terms "a" or "an" mean "at least one" or "one or more" unless the context clearly indicates otherwise.

As used herein, the term "about" means that the recited numerical vane is approximate and small variations would not significantly affect the practice of the disclosed embodiments. Where a numerical value is used, unless indicated otherwise by the context, "about" means the numerical value can vary by ±10% and remain within the scope of the disclosed embodiments.

As used herein, the term "animal" includes, but is not limited to, mammals, humans and non-human vertebrates, such as wild, domestic, and fam animas.

As used herein, the term "carrier" means a diluent, adjuvant, or excipient with which a compound is administered in a composition.

As used herein, the terms "comprising" (and any form of comprising, such as "comprise", "comprises", and "comprised"), "having" (and any form of having, such as "have" and "has"), "including" (and any form of including, such as "includes" and "include"), or "containing" (and any form of containing, such as "contains" and "contain"), are inclusive and open-ended and include the options following the terms, and do not exclude additional, unrecited elements or method steps.

As used herein, the terms "individual," "subject," and "patient," used interchangeably, mean any animal described herein.

As used herein, the phrase "in need thereof" means that the "individual," "subject," or "patient" has been identified as having a specific need for the particular method, prevention, or treatment. In some embodiments, the identification can be by any means of diagnosis. In any of the methods, preventions, and treatments described herein, the "individual," "subject," or "patient" can be in need thereof.

As used herein, the term "mammal" means a rodent (i.e, a mouse, a rat, or a guinea pig), a monkey, a sheep, a cat, a dog, a cow, a horse, a pig, or a human. In some embodiments, the mammal is a human.

As used herein, the phrase "pharmaceutically acceptable" means that the compounds, materials, compositions, and/or dosage forms are within the scope of sound medical judgment and are suitable for use in contact with tissues of humans and other animals. In some embodiments, "pharmaceutically acceptable" means approved by a regulatory agency of the Federal government or a state government or listed in the U.S. Pharmacopeia or other generally recognized pharmacopeia for use in animals, and more particularly in humans. In some embodiments, the pharmaceutically acceptable compounds, materials, compositions, and/or dosage forms result in no persistent detrimental effect on the subject, or on the general health of the subject being treated. However, it will be recognized that transient effects, such as minor irritation or a "stinging" sensation, are common with administration of medicament and the existence of such transient effects is not inconsistent with the composition, formulation, or ingredient (e.g., excipient) in question.

As used herein, the phrase "pharmaceutically acceptable salt(s)," includes, but is not limited to, salts of acidic or basic groups. Compounds that are basic in nature are capable of forming a wide variety of salts with various inorganic and organic acids. Acids that may be used to prepare pharmaceutically acceptable acid addition salts of such basic compounds are those that form non-toxic acid addition salts, i.e., salts containing pharmacologically acceptable anions including, but not limited to, sulfuric, thiosulfuric, citric, malic, maleic, acetic, oxalic, hydrochloride, hydrobromide, hydroiodide, nitrate, sulfate, bisulfate, bisulfite, phosphate, acid phosphate, isonicotinate, borate, acetate, lactate, salicylate, citrate, acid citrate, tartrate, oleate, tannate, pantothenate, bitartrate, ascorbate, succinate, malate, maleate, gentisinate, fumarate, gluconate, glucaronate, saccharate, formate, benzoate, glutamate, methanesulfonate, ethanesulfonate, benzenesulfonate, p-toluenesulfonate, bicarbonate, malonate, mesylate, esylate, napsydisylate, tosylate, besylate, orthophosphate, trifluoroacetate, and pamoate (i.e., 1,1-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include, but are not limited to, alkali metal or alkaline earth metal salts and, particularly, calcium, magnesium, ammonium, sodium, lithium, zinc, potassium, and iron salts. Salts also includes quaternary ammonium salts of the compounds described herein, where the compounds have one or more tertiary amine moiety.

As used herein, the phrase "therapeutically effective amount" means the amount of active compound or pharmaceutical agent that elicits the biological or medicinal response that is being sought in a tissue, system, animal, individual or human by a researcher, veterinarian, medical doctor, or other clinician. The therapeutic effect is dependent upon the disorder being treated or the biological effect desired. As such, the therapeutic effect can be a decrease in the severity of symptoms associated with the disorder and/or inhibition (partial or complete) of progression of the disorder, or improved treatment, healing, prevention or elimination of a disorder, or side-effects. The amount needed to elicit the therapeutic response can be based on, for example, the age, health, size, and sex of the subject. Optimal amounts can also be determined based on monitoring of the subject's response to treatment.

As used herein, the terms "treat," "treated," or"treating" mean both therapeutic treatment and prophylactic or preventative measures wherein the object is to prevent or slow down (lessen) an undesired physiological condition, disorder or disease, or obtain beneficial or desired clinical results.

For purposes herein, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state or remission (whether partial or total), whether detectable or undetectable; an amelioration of at least one measurable physical parameter, not necessarily discernible by the patient; or enhancement or improvement of condition, disorder or disease. Treatment includes eliciting a clinically significant response, optionally without excessive levels of side effects. Treatment also includes prolonging survival as compared to expected survival if not receiving treatment.

It should be appreciated that particular features of the disclosure, which are, for clarity, described in the context of separate embodiments, can also be provided in combination in a single embodiment. Conversely, various features of the disclosure which are, for brevity, described in the context of a single embodiment, can also be provided separately or in any suitable subcombination.

It should be understood that stereoisomers (including diastereomers and enantiomers) of the compounds described herein, as well as mixtures thereof are within the scope of the present disclosure. By way of non-limiting example, the mixture may be a racemate or the mixture may comprise unequal proportions of one particular stereoisomer over the other. Additionally, the compounds can be provided as substantially pure stereoisomers. Diastereomers include, for example, cis-trans isomers, E-Z isomers, conformers, and rotamers. Methods of preparation of stereoisomers are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds are also included within the scope of the invention and can be isolated as a mixture of isomers or as separated isomeric forms. Where a compound capable of stereoisomerism or geometric isomerism is designated in its structure or name without reference to specific R/S or cis/trans configurations, it is intended that all such isomers are contemplated.

Appropriate compounds described herein may also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Examples of prototropic tautomers include, but are not limited to, ketone-enol pairs, amide-imidic acid pairs, lactam-lactim pairs, amide-imidic acid pairs, enamine-imine pairs, and annular forms where a proton can occupy two more positions of a heterocyclic system including, but not limited to, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

The compounds described herein also include hydrates and solvates, as well as anhydrous and non-solvated forms.

The compounds described herein also include derivatives referred to as prodrugs, which can be prepared by modifying functional groups present in the compounds in such a way that the modifications are cleaved, either in routine manipulation or in vivo, to the parent compounds. Examples of prodrugs include compounds as described herein that contain one or more molecular moieties appended to a hydroxyl, amino, sulfhydryl, or carboxyl group of the compound, and that when administered to a patient, cleaves in vivo to form the free hydroxyl, amino, sulfhydryl, or carboxyl group, respectively. Examples of prodrugs include, but are not limited to, acetate, formate and benzoate derivatives of alcohol and amine functional groups in the compounds described herein. Preparation and use of prodrugs is discussed in T. Higuchi et al., "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are incorporated herein by reference in their entireties.

The present disclosure provides pharmaceutical compositions comprising a tyrosine kinase inhibitor chosen from sunitinib, axitinib, sorafenib, and erlotinib, or a pharmaceutically acceptable salt thereof; a farnesyltransferase inhibitor chosen from lonafarnib and tipifarnib, or a pharmaceutically acceptable salt thereof; and a pharmaceutically acceptable carrier. In some embodiments, the tyrosine kinase inhibitor is sunitinib, or a pharmaceutically acceptable salt thereof. In some embodiments, the tyrosine kinase inhibitor is sunitinib malate. In some embodiments, the farnesyltransferase inhibitor is lonafarnib, or a pharmaceutically acceptable salt thereof.

In some embodiments, the ratio of the tyrosine kinase inhibitor to the farnesyltransferase inhibitor is from about 0.01:1 to about 100:1 (w/w), from about 0.1:1 to about 10:1 (w/w), or from about 1:1 to about 5:1 (w/w). In some embodiments, the ratio of the tyrosine kinase inhibitor to the farnesyltransferase inhibitor is from about 0.01:1 to about 100:1 (w/w). In some embodiments, the ratio of the tyrosine kinase inhibitor to the farnesyltransferase inhibitor is from about 0.1:1 to about 10:1 (w/w). In some embodiments, the ratio of the tyrosine kinase inhibitor to the farnesyltransferase inhibitor is from about 1:1 to about 5:1 (w/w).

In some embodiments, the tyrosine kinase inhibitor is present in an amount from about 1 mg to about 100 mg, from about 5 mg to about 75 mg, from about 10 mg to about 60 mg, or from about 12.5 mg to about 50 mg, and the farnesyltransferase inhibitor is present in an amount from about 1 mg to about 500 mg, from about 50 mg to about 400 mg, from about 75 mg to about 300 mg, or from about 100 mg to about 200 mg. In some embodiments, the tyrosine kinase inhibitor is present in an amount from about 1 mg to about 100 mg. In some embodiments, the tyrosine kinase inhibitor is present in an amount from about 5 mg to about 75 mg. In some embodiments, the tyrosine kinase inhibitor is present in an amount from about 10 mg to about 60 mg. In some embodiments, the tyrosine kinase inhibitor is present in an amount from about 12.5 mg to about 50 mg. In some embodiments, the farnesyltransferase inhibitor is present in an amount from about 1 mg to about 500 mg. In some embodiments, the farnesyltransferase inhibitor is present in an amount from about 50 mg to about 400 mg. In some embodiments, the farnesyltransferase inhibitor is present in an amount from about 75 mg to about 300 mg. In some embodiments, the farnesyltransferase inhibitor is present in an mount from about 100 mg to about 200 mg.

In some embodiments, the pharmaceutical composition is an oral dosage form, an intravenous dosage form, a topical dosage form, an intraperitoneal dosage form, or an intrathecal dosage form. In some embodiments, the pharmaceutical composition is an oral dosage form or an intravenous dosage form. In some embodiments, the pharmaceutical composition is an oral dosage form.

In some embodiments, the oral dosage form is a pill, tablet, capsule, cachet, gel-cap, pellet, powder, granule, or liquid. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

In some embodiments, the oral dosage form comprises about 12.5 mg, about 25 mg, about 37.5 mg, or about 50 mg of the tyrosine kinase inhibitor. In some embodiments, the oral dosage form comprises about 12.5 mg of the tyrosine kinase inhibitor. In some embodiments, the oral dosage form comprises about 25 mg of the tyrosine kinase inhibitor. In some embodiments, the oral dosage form comprises about 37.5 mg of the tyrosine kinase inhibitor. In some embodiments, the oral dosage form comprises about 50 mg of the tyrosine kinase inhibitor.

In some embodiments, the oral dosage form comprises about 25 ng, about 50 mg, about 75 mg, about 100 mg, about 150 mg, or about 200 mg of the farnesyltransferase inhibitor. In some embodiments, the oral dosage form comprises about 25 mg of the farnesyltransferase inhibitor. In some embodiments, the oral dosage form comprises about 50 mg of the farnesyltransferase inhibitor. In some embodiments, the oral dosage form comprises about 75 mg of the farnesyltransferase inhibitor. In some embodiments, the oral dosage form comprises about 100 mg of the farnesyltransferase inhibitor. In some embodiments, the oral dosage form comprises about 150 mg of the farnesyltransferase inhibitor. In some embodiments, the oral dosage form comprises about 200 mg of the farnesyltransferase inhibitor.

In some embodiments, the oral dosage form is protected from light and present within a blister pack, bottle, or intravenous bag. In some embodiments, the oral dosage form is present within a blister pack, bottle, or intravenous bag. In some embodiments, the oral dosage form is present within a blister pack. In some embodiments, the oral dosage form is present within a bottle. In some embodiments, the oral dosage form is present within an intravenous bag.

The present disclosure also provides methods of treating cancer in a subject in need thereof comprising: administering to the subject a tyrosine kinase inhibitor chosen from sunitinib, axitinib, sorafenib, and erlotinib, or a pharmaceutically acceptable salt thereof; and administering to the subject a farnesyltransferase inhibitor chosen from lonafarnib and tipifarnib, or a pharmaceutically acceptable salt thereof. In some embodiments, the tyrosine kinase inhibitor is sunitinib, or a pharmaceutically acceptable salt thereof. In some embodiments, the tyrosine kinase inhibitor is sunitinib malate. In some embodiments, the farnesyltransferase inhibitor is lonafarnib, or a pharmaceutically acceptable salt thereof.

In some embodiments, the ratio of the administered tyrosine kinase inhibitor to the farnesyltransferase inhibitor is from about 0.01:1 to about 100:1 (w/w), from about 0.1:1 to about 10:1(w/w), or from about 1:1 to about 5:1 (w/w). In some embodiments, the ratio of the administered tyrosine kinase inhibitor to the farnesyltransferase inhibitor is from about 0.01:1 to about 100:1 (w/w). In some embodiments, the ratio of the administered tyrosine kinase inhibitor to the farnesyltransferase inhibitor is from about 0.1:1 to about 10:1 (w/w). In some embodiments, the ratio of the administered tyrosine kinase inhibitor to the farnesyltransferase inhibitor is from about 1:1 to about 5:1 (w/w).

In some embodiments, the tyrosine kinase inhibitor is administered in an amount from about 1 mg to about 100 mg, from about 5 mg to about 75 mg, from about 10 mg to about 60 mg, or from about 12.5 mg to about 50 mg, and the farnesyltransferase inhibitor is administered in an amount from about 1 mg to about 500 mg, from about 50 mg to about 400 mg, from about 75 mg to about 300 mg, or from about 100 mg to about 200 mg. In some embodiments, the tyrosine kinase inhibitor is administered in an amount from about 1 mg to about 100 mg. In some embodiments, the tyrosine kinase inhibitor is administered in an amount from about 5 mg to about 75 mg. In some embodiments, the tyrosine kinase inhibitor is administered in an amount from about 10 mg to about 60 mg. In some embodiments, the tyrosine kinase inhibitor is administered in an amount from about 12.5 mg to about 50 mg. In some embodiments, the farnesyltransferase inhibitor is administered in an amount from about 1 mg to about 500 mg. In some embodiments, the farnesyltransferase inhibitor is administered in an amount from about 50 mg to about 400 mg. In some embodiments, the farnesyltransferase inhibitor is administered in an amount from about 75 mg to about 300 mg. In some embodiments, the farnesyltransferase inhibitor is administered in an amount from about 100 mg to about 200 mg.

In some embodiments, the tyrosine kinase inhibitor is administered prior to the administration of the farnesyltransferase inhibitor or after administration of the farnesyltransferase inhibitor. In some embodiments, the tyrosine kinase inhibitor is administered prior to the administration of the farnesyltransferase inhibitor. In some embodiments, the tyrosine kinase inhibitor is administered after administration of the farnesyltransferase inhibitor. In some embodiments, the tyrosine kinase inhibitor is administered concurrently with administration of the farnesyltransferase inhibitor.

In some embodiments, the tyrosine kinase inhibitor is present in a pharmaceutical composition which is an oral dosage form, an intravenous dosage form, a topical dosage form, an intraperitoneal dosage form, or an intrathecal dosage form. In some embodiments, the tyrosine kinase inhibitor is present in a pharmaceutical composition which is an oral dosage form or an intravenous dosage form. In some embodiments, the tyrosine kinase inhibitor is present in a pharmaceutical composition which is an oral dosage form. In some embodiments, the oral dosage form is a pill, tablet, capsule, cachet, gel-cap, pellet, powder, granule, or liquid. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

In some embodiments, the oral dosage form comprises about 12.5 mg, about 25 mg, about 37.5 mg, or about 50 mg of the tyrosine kinase inhibitor. In some embodiments, the oral dosage form comprises about 12.5 mg of the tyrosine kinase inhibitor. In some embodiments, the oral dosage form comprises about 25 mg of the tyrosine kinase inhibitor. In some embodiments, the oral dosage form comprises about 37.5 mg of the tyrosine kinase inhibitor. In some embodiments, the oral dosage form comprises about 50 mg of the tyrosine kinase inhibitor.

In some embodiments, the farnesyltransferase inhibitor is present in a pharmaceutical composition which is an oral dosage form, an intravenous dosage form, a topical dosage form, an intraperitoneal dosage form, or an intrathecal dosage form. In some embodiments, the farnesyltransferase inhibitor is present in a pharmaceutical composition which is an oral dosage form or an intravenous dosage form. In some embodiments, the farnesyltransferase inhibitor is present in a pharmaceutical composition which is an oral dosage form. In some embodiments, the oral dosage form is a pill, tablet, capsule, cachet, gel-cap, pellet, powder, granule, or liquid. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

In some embodiments, the oral dosage form comprises about 25 mg, about 50 mg, about 75 mg, about 100 mg, about 150 mg, or about 200 mg of the farnesyltransferase inhibitor. In some embodiments, the oral dosage form comprises about 25 mg of the farnesyltransferase inhibitor. In some embodiments, the oral dosage form comprises about 50 mg of the farnesyltransferase inhibitor. In some embodiments, the oral dosage form comprises about 75 mg of the farnesyltransferase inhibitor. In some embodiments, the oral dosage form comprises about 100 mg of the farnesyltransferase inhibitor. In some embodiments, the oral dosage form comprises about 150 mg of the farnesyltransferase inhibitor. In some embodiments, the oral dosage form comprises about 200 mg of the farnesyltransferase inhibitor.

In some embodiments, the tyrosine kinase inhibitor and the farnesyltransferase inhibitor are administered to the subject together in a single pharmaceutical composition. In some embodiments, the single pharmaceutical composition is an oral dosage form, an intravenous dosage form, a topical dosage form, an intraperitoneal dosage form, or an intrathecal dosage form. In some embodiments, the single pharmaceutical composition is an oral dosage form or an intravenous dosage form. In some embodiments, the single pharmaceutical composition is an oral dosage form. In some embodiments, the single pharmaceutical composition is an intravenous dosage form. In some embodiments, the oral dosage form is a pill, tablet, capsule, gel-cap, or liquid. In some embodiments, the oral dosage form is a pill. In some embodiments, the oral dosage form is a tablet. In some embodiments, the oral dosage form is a capsule. In some embodiments, the oral dosage form is a gel-cap. In some embodiments, the oral dosage form is a liquid.

In some embodiments, the single pharmaceutical composition comprises about 12.5 mg, about 25 mg, about 37.5 mg, or about 50 mg of the tyrosine kinase inhibitor. In some embodiments, the single pharmaceutical composition comprises about 12.5 mg of the tyrosine kinase inhibitor. In some embodiments, the single pharmaceutical composition comprises about 25 mg of the tyrosine kinase inhibitor. In some embodiments, the single pharmaceutical composition comprises about 37.5 mg of the tyrosine kinase inhibitor. In some embodiments, the single pharmaceutical composition comprises about 50 mg of the tyrosine kinase inhibitor.

In some embodiments, the single pharmaceutical composition comprises about 25 mg, about 50 mg, about 75 mg, about 100 mg, about 150 mg, or about 200 mg of the farnesyltransferase inhibitor. In some embodiments, the single pharmaceutical composition comprises about 25 mg of the farnesyltransferase inhibitor. In some embodiments, the single pharmaceutical composition comprises about 50 mg of the farnesyltransferase inhibitor. In some embodiments, the single pharmaceutical composition comprises about 75 mg of the farnesyltransferase inhibitor. In some embodiments, the single pharmaceutical composition comprises about 100 mg of the farnesyltransferase inhibitor. In some embodiments, the single pharmaceutical composition comprises about 150 mg of the farnesyltransferase inhibitor. In some embodiments, the single pharmaceutical composition comprises about 200 mg of the farnesyltransferase inhibitor.

In some embodiments, the subject is also administered radiation therapy, immunotherapy, and/or neoadjuvant therapy. In some embodiments, the subject is also administered radiation therapy. In some embodiments, the subject is also administered immunotherapy. In some embodiments, the subject is also administered neoadjuvant therapy.

In some embodiments, the cancer is breast cancer, pancreatic cancer, prostate cancer, lung cancer, liver cancer, esophageal cancer, stomach cancer, biliary tract cancer, head and neck cancer, bladder cancer, kidney cancer, mesothelioma, thyroid cancer, uterine cancer, ovarian cancer, brain cancer, lymphoma, myeloma, leukemia, or colon cancer. In some embodiments, the cancer is kidney cancer. In some embodiments, the cancer is renal cell carcinoma, clear cell renal carcinoma (ccRCC), papillary renal cell carcinoma, chromophobe renal cell carcinoma, or unclassified renal cell carcinoma. In some embodiments, the cancer is renal cell carcinoma. In some embodiments, the cancer is clear cell renal carcinoma (ccRCC). In some embodiments, the cancer is papillary renal cell carcinoma. In some embodiments, the cancer is chromophobe renal cell carcinoma. In some embodiments, the cancer is unclassified renal cell carcinoma.

The compounds and compositions described herein can be administered by any route of administration including, but not limited to, oral, intravenous, topical, intraperitoneal, and intrathecal. In some embodiments, the administration is oral, intravenous, intraperitoneal, or intrathecal. In some embodiments, the administration is oral, intravenous, or intraperitoneal. In some embodiments, the administration is oral or intravenous. In some embodiments, the administration is oral or topical. In some embodiments, the administration is oral or intraperitoneal. In some embodiments, the administration is oral or intrathecal. The route of administration can depend on the particular disease, disorder, or condition being treated and can be selected or adjusted by the clinician according to methods known to the clinician to obtain desired clinical responses. Methods for administration are known in the art and one skilled in the art can refer to various pharmacologic references for guidance (see, for example, Modern Pharmaceutics, Banker & Rhodes, Marcel Dekker, Inc. (1979); and Goodman & Gilman's The Pharmaceutical Basis of Therapeutics, 6th Edition, MacMillan Publishing Co., New York (1980)).

In some embodiments, it may be desirable to administer one or more compounds, or a pharmaceutically acceptable salt thereof, or composition(s) comprising the same to a particular area in need of treatment. This may be achieved, for example, by local infusion (for example, during surgery), topical application (for example, with a wound dressing after surgery), or by injection (for example, by depot injection). Formulations for injection can be presented in unit dosage form, such as in ampoules or in multi-dose containers, with an added preservative.

The compounds and compositions described herein can be formulated for parenteral administration by injection, such as by bolus injection or continuous infusion. The compounds and compositions can be administered by continuous infusion subcutaneously over a period of about 15 minutes to about 24 hours. The compositions can take such forms as suspensions, solutions or emulsions in oily or aqueous vehicles, and can contain formulatory agents such as suspending, stabilizing and/or dispersing agents. In some embodiments, the injectable is in the form of short-acting, depot, or implant and pellet forms injected subcutaneously or intramuscularly. In some embodiments, the parenteral dosage form is the form of a solution, suspension, emulsion, or dry powder.

For oral administration, the compounds and compositions described herein can be formulated by combining the compounds with pharmaceutically acceptable carriers. Such carriers enable the compounds to be formulated as tablets, pills, dragees, capsules, emulsions, liquids, gels, syrups, caches, pellets, powders, granules, slurries, lozenges, aqueous or oily suspensions, and the like, for oral ingestion by a subject to be treated. Pharmaceutical preparations for oral use can be obtained by, for example, adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations including, but not limited to, maize starch, wheat starch, rice starch, potato starch, gelatin, gum tragacanth, methyl cellulose, hydroxypropylmethylcellulose, sodium carboxymethylcellulose, and polyvinylpyrrolidone (PVP). If desired, disintegrating agents can be added, including, but not limited to, the cross-linked polyvinyl pyrrolidone, agar, or alginic acid or a salt thereof such as sodium alginate.

Orally administered compounds and compositions can contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, when in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds. Oral compositions can include standard vehicles such as, for example, mannitol, lactose, starch, magnesium stearate, sodium saccharine, cellulose, magnesium carbonate, etc. Such vehicles are suitably of pharmaceutical grade.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added.

In transdermal administration, the compounds and compositions can be applied to a plaster, or can be applied by transdermal, therapeutic systems that are consequently supplied to the organism. In some embodiments, the compounds and compositions are present in creams, solutions, powders, fluid emulsions, fluid suspensions, semi-solids, ointments, pastes, gels, jellies, and foams, or in patches containing any of the same.

The compounds and compositions described herein can also be formulated as a depot preparation. Such long acting formulations can be administered by implantation (for example subcutaneously or intramuscularly) or by intramuscular injection. Depot injections can be administered at about 1 to about 6 months or longer intervals. Thus, for example, the compounds and compositions can be formulated with suitable polymeric or hydrophobic materials (for example as an emulsion in an acceptable oil) or ion exchange resins, or as sparingly soluble derivatives, for example, as a sparingly soluble salt.

In some embodiments, the compounds and compositions can be delivered in a controlled release system. In some embodiments, a pump may be used (see Langer, supra; Sefton, CRC Crit. Ref. Biomed. Eng., 1987, 14, 201; Buchwald et al., Surgery, 1980, 88, 507 Saudek et al., N. Engl. J. Med., 1989, 321, 574). In some embodiments, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger et al., J. Macromol. Sci. Rev. Macromol. Chem., 1983, 23, 61; see, also Levy et al., Science, 1985, 228, 190; During et al., Ann. Neurol., 1989, 25, 351; Howard et al., J. Neurosurg., 1989, 71, 105). In some embodiments, a controlled-release system can be placed in proximity of the target of the compounds described herein, such as the liver, thus requiring only a fraction of the systemic dose (see, e.g., Goodson, in Medical Applications of Controlled Release, supra, vol. 2, pp. 115-138 (1984)). Other controlled-release systems discussed in the review by Langer, Science, 1990, 249, 1527-1533) may be used.

The compounds and compositions described herein can be contained in formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The pharmaceutical compositions can also comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols. In some embodiments, the compounds described herein can be used with agents including, but not limited to, topical analgesics (e.g., lidocaine), barrier devices (e.g., GELCLAIR®), or rinses (e.g., CAPHOSOL®). Pharmaceutical carriers can be liquids, such as water and oils, including those of petroleum, animal, vegetable or synthetic origin, such as peanut oil, soybean oil, mineral oil, sesame oil, and the like. The pharmaceutical carriers can also be saline, gum acacia, gelatin, starch paste, talc, keratin, colloidal silica, urea, and the like. In addition, auxiliary, stabilizing, thickening, lubricating and coloring agents can be used.

In some embodiments, the compounds and compositions described herein can be delivered in a vesicle, in particular a liposome (see, Langer, Science, 1990, 249, 1527-1533; Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.).

The compositions described herein can be administered either alone (as a single composition comprising the compounds described herein) or in combination (concurrently or serially) with other pharmaceutical agents. For example, the compounds and compositions can be administered in combination with anti-cancer or anti-neoplastic agents (for example, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, camptothecins, bleomycin, doxorubicin, idarubicin, daunorubicin, dactinomycin, plicamycin, mitoxantrone, asparaginase, vinblastine, vincristine, vinorelbine, paclitaxel, and docetaxel) or therapies (for example, surgery or radiotherapy).

The amount of any particular compound to be administered may be that amount which is therapeutically effective. The dosage to be administered may depend on the characteristics of the subject being treated, e.g., the particular animal treated, age, weight, health, types of concurrent treatment, if any, and frequency of treatments, and on the nature and extent of the disease, condition, or disorder, and can be easily determined by one skilled in the art (e.g., by the clinician). The selection of the specific dose regimen can be selected or adjusted or titrated by the clinician according to methods known to the clinician to obtain the desired clinical response. In addition, in vitro or in view assays may optionally be employed to help identify optimal dosage ranges. The precise dose to be employed in the compositions may also depend on the route of administration, and should be decided according to the judgment of the practitioner and each patient's circumstances.

Suitable compositions include, but are not limited to, oral non-absorbed compositions. Suitable compositions also include, but are not limited to saline, water, cyclodextrin solutions, and buffered solutions of pH 3-9.

The compounds and compositions described herein can be formulated with numerous excipients including, but not limited to, purified water, propylene glycol, PEG 400, glycerin, DMA, ethanol, benzyl alcohol, citric acid/sodium citrate (pH3), citric acid/sodium citrate (pHS), tris(hydroxymethyl)amino methane HCl (pH7.0), 0.9% saline, and 1.2% saline, and any combination thereof. In some embodiments, excipient is chosen from propylene glycol, purified water, and glycerin.

In some embodiments, the excipient is a multi-component system chosen from 20% w/v propylene glycol in saline, 30% w/v propylene glycol in saline, 40% w/v propylene glycol in saline, 50% w/v propylene glycol in saline, 15% w/v propylene glycol in purified water, 30% w/v propylene glycol in purified water, 50% w/v propylene glycol in purified water, 30% w/v propylene glycol and 5 w/v ethanol in purified water, 15% w/v glycerin in purified water, 30% w/v glycerin in purified water, 50% w/v glycerin in purified water, 20% w/v KLEPTOSE® in purified water, 40% w/v KLEPTOSE® in purified water, and 25% w/v CAPTISOL® in purified water. In some embodiments, the excipient is chosen from 50% w/v propylene glycol in purified water, 15% w/v glycerin in purified water, 20% w/v KLEPTOSE® in purified water, 40% w/v KLEPTOSE® in purified water, and 25% w/v CAPTISOL® in purified water. In some embodiments, the excipient is chosen from 20% w/v KLEPTOSE® in purified water, 20% w/v propylene glycol in purified water, and 15% w/v glycerin in purified water.

In some embodiments, the compounds and compositions described herein can be lyophilized to a solid and reconstituted with, for example, water prior to use.

When administered to a human, the compounds and compositions can be sterile. Water is a suitable carrier when the compound and composition is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The compositions described herein can take the form of a solution, suspension, emulsion, tablet, pill, pellet, capsule, capsule containing a liquid, powder, sustained-release formulation, aerosol, spray, or any other form suitable for use. Examples of suitable pharmaceutical carriers are described in Remington's Pharmaceutical Sciences, A. R. Gennaro (Editor) Mack Publishing Co.

In some embodiments, the compounds and compositions are formulated in accordance with routine procedures as pharmaceutical compositions adapted for administration to humans. Typically, compounds are solutions in sterile isotonic aqueous buffer. Where necessary, the compositions can also include a solubilizing agent. Compositions for intravenous administration may optionally include a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the compound or composition is to be administered by infusion, it can be dispensed, for example, with an infusion bottle containing sterile pharmaceutical grade water or saline. Where the compound or composition is administered by injection, an ampoule of sterile water for injection or saline can be provided so that the ingredients may be mixed prior to administration.

The pharmaceutical compositions can be in unit dosage form. In such form, the composition can be divided into unit doses containing appropriate quantities of the active component. The unit dosage form can be a packaged preparation, the package containing discrete quantities of the preparations, for example, packeted tablets, capsules, and powders in vials or ampules. The unit dosage form can also be a capsule, cachet, or tablet itself, or it can be the appropriate number of any of these packaged forms.

In some embodiments, a composition of the present invention is in the form of a liquid wherein the active agents are present in solution, in suspension, as an emulsion, or as a solution/suspension. In some embodiments, the liquid composition is in the form of a gel. In other embodiments, the liquid composition is aqueous. In other embodiments, the composition is in the form of an ointment.

In some embodiments, the composition is an in situ gellable aqueous solution, suspension or solution/suspension, comprising about from 0.2% to about 3% or from about 0.5% to about 1% by weight of a gelling polysaccharide, chosen from gellan gum, alginate gum and chitosan, and about 1% to about 50% of a water-soluble film-forming polymer, preferably selected from alkylcelluloses (e.g., methylcelluose, ethylcellulose), hydroxyalkylcelluloses (e.g., hydroxyethylcellulose, hydroxypropyl methylcellulose), hyaluronic acid and salts thereof, chondroitin sulfate and salts thereof polymers of acrylamide, acrylic acid and polycyanoacrylates, polymers of methyl methacrylate and 2-hydroxyethyl methacrylate, polydextrose, cyclodextrins, polydextrin, maltodextrin, dextran, polydextrose, gelatin, collagen, natural gums (e.g., xanthan, locust bean, acacia, tragacanth and carageenan gums and agar), polygalacturonic acid derivatives (e.g., pectin), polyvinyl alcohol, polyvinylpyrrolidone and polyethylene glycol. The composition can optionally contain a gel-promoting counterion such as calcium in latent form, for example encapsulated in gelatin.

In yet other embodiments, the composition is an in situ gellable aqueous solution, suspension or solution/suspension comprising about 0.1% to about 5% of a carrageenan gum, e.g., a carrageenan gum having no more than 2 sulfate groups per repeating disaccharide unit, such as e.g., kappa-carrageenan, having 18-25% ester sulfate by weight, iota-carrageenan, having 25-34% ester sulfate by weight, and mixtures thereof.

Optionally one or more stabilizers can be included in the compositions to enhance chemical stability where required. Suitable stabilizers include, but are not limited to, chelating agents or complexing agents, such as, for example, the calcium complexing agent ethylene diamine tetraacetic acid (EDTA). For example, an appropriate amount of EDTA or a salt thereof, e.g., the disodium salt, can be included in the composition to complex excess calcium ions and prevent gel formation during storage. EDTA or a salt thereof can suitably be included in an amount of about 0.01% to about 0.5%. In those embodiments containing a preservative other than EDTA, the EDTA or a salt thereof, more particularly disodium EDTA, can be present in an amount of about 0.025% to about 0.1% by weight.

The present disclosure also provides combinations of a tyrosine kinase inhibitor chosen from sunitinib, axitinib, sorafenib, and erlotinib, or a pharmaceutically acceptable salt thereof, and a farnesyltransferase inhibitor chosen from lonafarnib and tipifarnib, or a pharmaceutically acceptable salt thereof, for use in the manufacture of a medicament for treating cancer. Any of the combinations described herein can be used in the manufacture of a medicament for treating any of the cancers described herein.

The present disclosure also provides uses of a pharmaceutical composition comprising a tyrosine kinase inhibitor chosen from sunitinib, axitinib, sorafenib, and erlotinib, or a pharmaceutically acceptable salt thereof, and a farnesyltransferase inhibitor chosen from lonafarnib and tipifarnib, or a pharmaceutically acceptable salt thereof, for treating cancer. Any of the combinations described herein can be used for treating any of the cancers described herein.

The present disclosure also provides methods of treating or reducing a cancer, inhibiting tumor growth, or treating or preventing spread or metastasis of cancer (e.g., any of the cancers described herein) in a mammal comprising administering to the mammal in need thereof any of the combinations of compounds, or compositions comprising the same as described herein. In some embodiments, one or more compounds may be combined in the same composition for any of the methods disclosed herein.

The present disclosure also provides methods for killing or inhibiting growth of a cancer cell comprising contacting the cancer cell with any of the combinations of compounds, or compositions comprising the same as described herein. In some embodiments, one or more compounds may be combined in the same composition for any of the methods disclosed herein.

Thus, the compounds and compositions can be used as anti-cancer and anti-tumor agents, e.g., the compounds can kill or inhibit the growth of cancer cells. The compounds and compositions can also be used in methods of reducing cancer in an animal, or in methods of treating or preventing the spread or metastasis of cancer in an animal, or in methods of treating an animal afflicted with cancer. The compounds and compositions can also be used in methods of killing or inhibiting the growth of a cancer cell, or in methods of inhibiting tumor growth.

Generally, cancer refers to any malignant growth or tumor caused by abnormal and uncontrolled cell division; it may spread to other pats of the body through the lymphatic system or the blood stream. Cancers include both solid tumors and blood-borne tumors. Cancers that are treatable are broadly divided into the categories of carcinoma, lymphoma and sarcoma. Examples of carcinomas include, but are not limited to: adenocarcinoma, acinic cell adenocarcinoma, adrenal cortical carcinomas, alveoli cell carcinoma, anaplastic carcinoma, basaloid carcinoma, basal cell carcinoma, bronchiolar carcinoma, bronchogenic carcinoma, renaladinol carcinoma, embryonal carcinoma, anometroid carcinoma, fibrolamolar liver cell carcinoma, follicular carcinomas, giant cell carcinomas, hepatocellular carcinoma, intraepidermal carcinoma, intraepithelial carcinoma, leptomanigio carcinoma, medullary carcinoma, melanotic carcinoma, menigual carcinoma, mesometonephric carcinoma, oat cell carcinoma, squamal cell carcinoma, sweat gland carcinoma, transitional cell carcinoma, and tubular cell carcinoma. Sarcomas include, but are not limited to: amelioblastic sarcoma, angiolithic sarcoma, botryoid sarcoma, endometrial stroma sarcoma, ewing sarcoma, fascicular sarcoma, giant cell sarcoma, granulositic sarcoma, immunoblastic sarcoma, juxaccordial osteogenic sarcoma, coppices sarcoma, leukocytic sarcoma (leukemia), lymphatic sarcoma (lympho sarcoma), medullary sarcoma, myeloid sarcoma (graulocitic sarcoma), anstiogenci sarcoma, periosteal sarcoma, reticulum cell sarcoma (histiocytic lymphoma), round cell sarcoma, spindle cell sarcoma, synovial sarcoma, and telangiectatic audiogenic sarcoma. Lymphomas include, but are not limited to: Hodgkin's disease and lymphocytic lymphomas, such as Burkitt's lymphoma, NPDL, NML, NH and diffuse lymphomas.

Examples of cancers that can be treated using the compounds described herein include, but are not limited to, Hodgkin's disease, non-Hodgkin's lymphomas, acute lymphocytic leukemia, multiple myeloma, breast carcinomas, ovarian carcinomas, lung carcinomas, Wilms' tumor, testicular carcinomas, soft-tissue sarcomas, chronic lymphocytic leukemia, primary macroglobulinemia, bladder carcinomas, chronic granulocytic leukemia, primary brain carcinomas, malignant melanoma, small-cell lung carcinomas, stomach carcinomas, colon carcinomas, malignant pancreatic insulinoma, malignant carcinoid carcinomas, malignant melanomas, choriocarcinomas, mycosis fungoides, head and neck carcinomas, osteogenic sarcoma, pancreatic carcinomas, acute granulocytic leukemia, hairy cell leukemia, rhabdomyosarcoma, Kaposi's sarcoma, genitourinary carcinomas, thyroid carcinomas, esophageal carcinomas, malignant hypercalcemia, renal cell carcinomas, endometrial carcinomas, polycythemia vera, essential thrombocytosis, adrenal cortex carcinomas, skin cancer, and prostatic carcinomas.

In some embodiments, the cancer is lung cancer (such as non-small cell lung cancer), breast cancer, prostate cancer, ovarian cancer, testicular cancer, colon cancer, renal cancer, bladder cancer, pancreatic cancer, glioblastoma, neuroblastoma, sarcomas such as Kaposi's sarcoma and Ewing's sarcoma, hemangiomas, solid tumors, blood-borne tumors, rhabdomyosarcoma, CNS cancer (such as brain cancer), retinoblastoma, neuroblastoma, leukemia, melanoma, kidney or renal cancer, and osteosarcoma.

The compounds and compositions can be used in methods of killing or inhibiting the growth of cancer cells, either in vivo or In vitro, or inhibiting the growth of a cancerous tumor.

In some embodiments, the compounds and compositions are used in conjunction with other therapies, such as standard immunotherapy, neoadjuvant therapy, radiotherapy, tumor surgery, and conventional chemotherapy directed against solid tumors and for the control of establishment of metastases. Additionally, the compounds and compositions can be administered after surgery where solid tumors have been removed as a prophylaxis against metastasis. Cytotoxic or chemotherapeutic agents include, but are of limited to, aziridine thiotepa, alkyl sulfonate, nitrosoureas, platinum complexes, NO classic alkylators, folate analogs, purine analogs, adenosine analogs, pyrimidine analogs, substituted urea, antitumor antibiotics, microtubulle agents, and asprignase.

In order that the subject matter disclosed herein may be more efficiently understood, examples are provided below. It should be understood that these examples are for illustrative purposes only and are not to be construed as limiting the claimed subject matter in any manner.

EXAMPLES

Example 1: CRISPR/Cas9-Based Genome-Wide LOF Screening to Identify Cellular Factors Contributing to Sunitinib Resistance in RCC The RNA-guided CRISPR-associated nuclease Cas9 provides an effective means of introducing targeted loss-of-function mutations at specific sites in the genome. For lentiviral production, 293T cells were transfected with pCW-Cas9 (encoding FLAG-tagged Cas9 nuclease driven by doxycycline-inducible promoter and puromycin resistance marker), pVSV-G and psPAX2 vectors. 786-O RCC cells were infected with lentivirus at high multiplicity of infection (MOI). After selection of infected cells with puromycin, several individual clones were analyzed. A clone with superior Cas9 induction rate was selected and subjected to the infection with lentiviral LOF sgRNA library (containing blasticidin resistance marker) at low MOI<1. The library was selected with 10 μg/ml of blasticidine and frozen for future manipulations.

Figure 2:
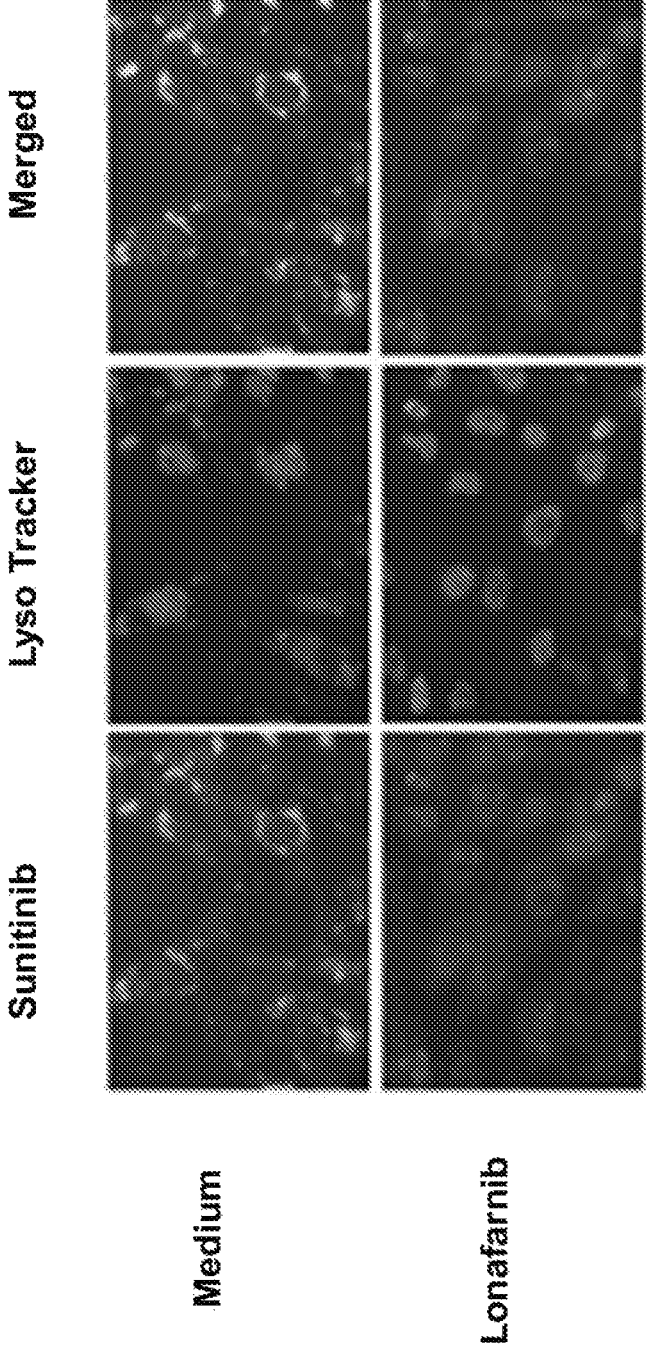
FIG. 2 depicts lysosomal sequestration of sunitinib examined by fluorescent microscopy.

To identify genes contributing to sunitinib resistance, lentiviral delivery of sgRNA library targeting 18,000 genes with 90,000 individual sgRNAs (5 sgRNA per one gene) was carried out. A brief overview of this method is depicted in FIG. 1. Sunitinib-resistant 786-O RCC cells were incubated with sunitinib (10 μM) for 12 days (six passages in culture). During this time, the cells with the knockout genes which contribute to the resistance to sunitinib were eliminated from the population. Next, underrepresented sgRNAs and their corresponding gene targets in the surviving cell population were identified. The primers corresponding to sequences flanking the guide in the lentiviral vector included 8-bp bar codes for Illumina-based sequencing. Thus, each sgRNA served as an individual DNA barcode that was used to count the number of cells carrying guides by sequencing. The search identified a number of genes potentially involved in sunitinib resistance in RCC. Based on the highest rank of identified genes, the identified genes were selected, which have not been previously reported to be involved in TKI resistance (encoding FTase, RABGGTase, their effectors (RAB7a, RAB25, RhoB and Rheb) and LAMP2). The subcellular localization of sunitinib can be disrupted by lonafarnib. Treatment with lonafarnib significantly reduced sequestration of sunitinib within lysosomes (see, FIG. 2). In particular, FIG. 2 shows the results of lysosomal sequestration of sunitinib examined by fluorescent microscopy. 786-O cells were cultured in medium only or in the presence of lonafarnib (5 mM) overnight followed by treatment with 10 mM sunitinib (green), 75 nM LYSOTRACKER® (red), and 1 mg/mL Hoechst (blue) for 60 minutes. In cells cultured in medium only sunitinib and LYSOTRACKER® were found to be highly colocalized (yellow). Treatment with lonafarnib significantly reduced sequestration of sunitinib within lysosomes. Importantly, the total cellular accumulation of sunitinib was not affected by lonafarnib (data not shown).

Figure 3:
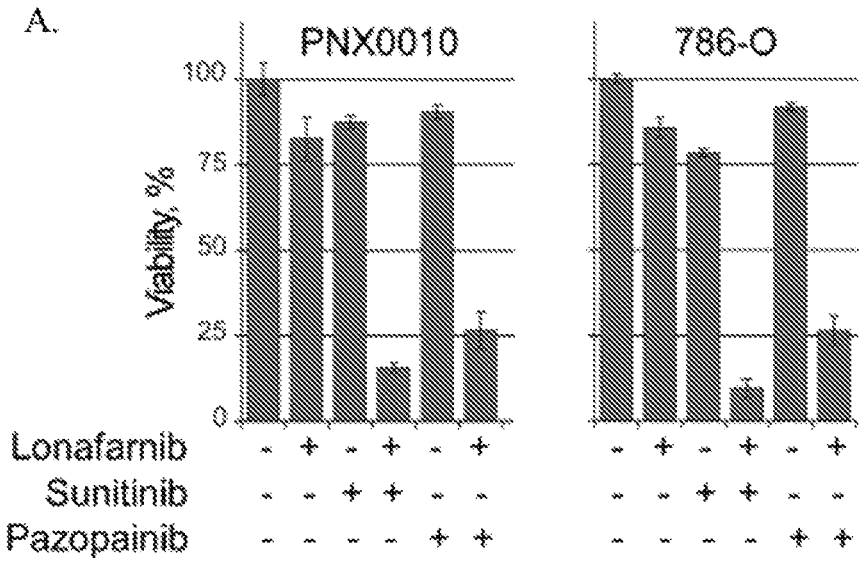
FIG. 3 shows pharmacological inhibition of FTase enhances the antitumor activity of sunitinib and cell viability examined using a CELLTITER-BLUE® assay (Panel A), and DNA fragmentation followed by flow cytometry analysis (Panel B).
Figure 3:
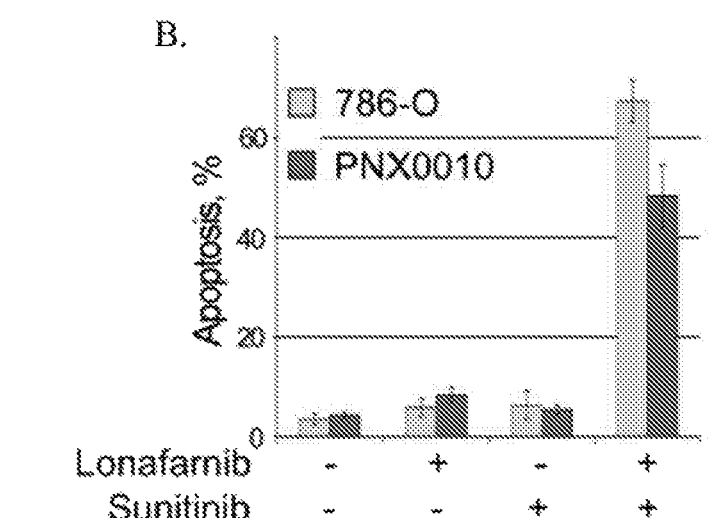

Treatment with lonafarnib can reinstate sensitivity of RCC cells to TKIs. Pharmacological inhibition of FTase enhances the antitumor activity of sunitinib. Referring to FIG. 3, in Panel A, PNX0010 and 786-O RCC cells were treated with various combinations of lonafarnib (2 mM), sunitinib (1.5 mM), and pazopanib (1.5 mM) for 72 hours. Cell viability was examined using Blue CELLTITER-BLUE® assay (PROMEGA®). In Panel B, 786-O and PNX0010 RCC cells were treated with lonafarnib (5 mM) and/or sunitinib (10 mM) for 24 hours. DNA fragmentation was examined by the APO-BRDU kit (The Phoenix Flow Systems) followed by flow cytometry analysis. As demonstrated in FIG. 3, Panel A, treatment with either sunitinib or lonafarnib had a modest effect on viability of established 786-O and patient-derived PNX0010 RCC cells. In contrast, combined treatment resulted in a marked loss of viability of 786-O and PNX0010 cells. Similar results were obtained with another TKI conventionally used for the treatment of RCC patients, pazopanib. These data suggest that the inhibition of FTase may be a common strategy to improve the antitumor activity of TKIs. Concomitant treatment with lonafarnib and sunitinib at higher doses resulted in profound DNA fragmentation in 786-O and PNX0010 cells (see, FIG. 3, Panel B). The dose-dependent anti-proliferative effects of sunitinib, axitinib and lonafarnib were examined on 786-O cells. Table 1 demonstrates the range of Effective Doses for those drugs. The synergistic effects of sunitinib/lonafarnib or axitinib/lonafarnib combinational treatment on the viability of 786-O cells was also examined.

TABLE 1

| Dose response of 786-O cells to indicated drugs | | | |
| --- | --- | --- | --- |
| Drug | ED50 | ED75 | ED90 |
| Sunitinib | 2.4 μM | 6.7 μM | 44.3 μM |
| Axitinib | 1.9 μM | 7.5 μM | 65.1 μM |
| Lonafarnib | 3.8 μM | 63.3 μM | 5672.0 μM |

Excitingly, the data analysis using CalcuSyn 2.0 software revealed a strong synergy for all tested drugs (see, Table 2).

TABLE 2

| Combination Index (CI) values at Effective Doses (ED) for sunitinib/lonafarnib (Sut/LF) or axitinib/lonafarnib (Ax/LF) combinations at 1:1 ratio | | | |
| --- | --- | --- | --- |
| Drug | ED50 | ED75 | ED90 |
| Sut/LF comb 1.1 | 0.67953 | 0.15809 | 0.05165 |
| Ax/LF comb 1:1 | 0.42284 | 0.43371 | 0.51271 |

Figure 4:
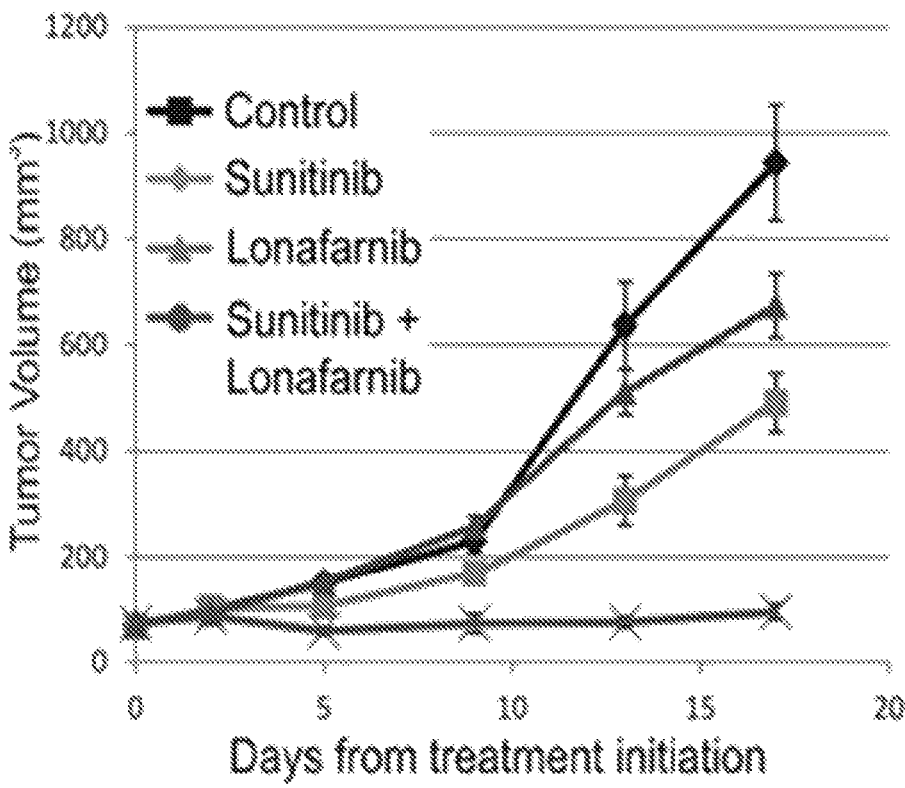
FIG. 4 shows lonafarnib enhances the antitumor activity of sunitinib in vivo.
Figure 5:
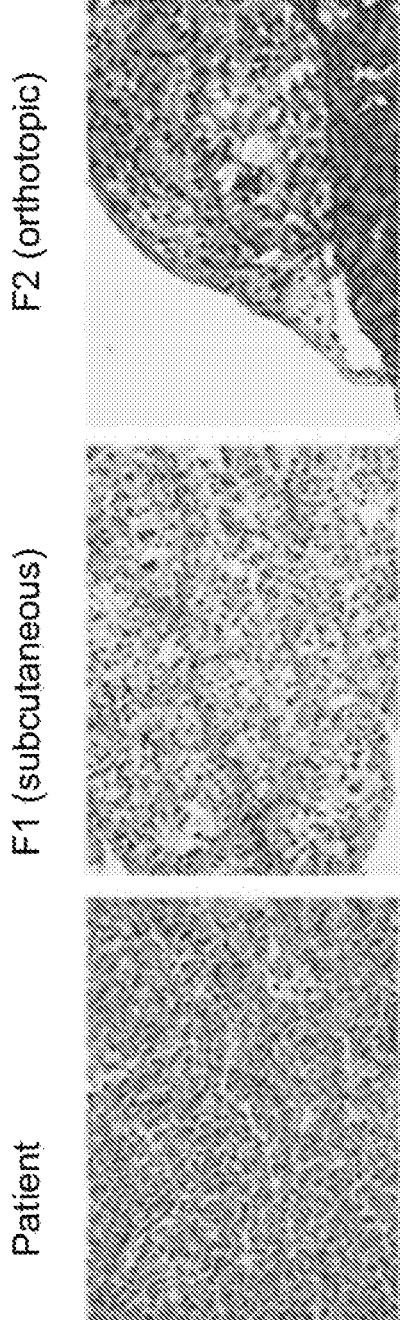
FIG. 5 shows representative H&E-stained sections of tumor tissue specimens; histological resemblance between the RCC patient tumor and resulting tumorgrafts (PNX0010).

In light of the encouraging in vitro data, the antitumor effects of sunitinib in combination with lonafarnib was examined using a mouse xenograft model bearing PNXC0010 RCC tumors. Lonafarnib enhanced the antitumor activity of sunitinib in vivo. PNX0010 subcutaneous xenografts were established in 6 week old male C.B17/lcrscid mice. The mice were treated orally 3 times/week with (i) 10% 2-hydroxypropyl-b-cyclodextrin in PBS (control); (ii) sunitinib (40 mg/kg); (iii) lonafarnib (40 mg/kg); or with sunitinib and lonafarnib combined (n=5 mice/group). Tumor volumes were calculated by the formula: (volume=0.52× (width)2×length). As demonstrated in FIG. 4, single agent treatment with sunitinib or lonafarnib showed a moderate decrease in the growth of xenograft tumors. However, combination treatment with sunitinib or lonafarnib resulted in vastly more impressive inhibition of tumor growth among the experimental groups. FIG. 5 shows representative H&E-stained sections of tumor tissue specimens; histological resemblance between the RCC patient tumor and resulting tumorgrafts (PNX0010). These results suggest a readily available clinical strategy to circumvent sunitinib resistance in RCC tumors.

Example 2: Mechanisms Underlying the Synergistic Antitumor Activity of TKI and FTIs (Prophetic Example)

The studies using CRISPR/Cas9-based genome-wide screening reveal a critical role of FTase and its effectors for the resistance of RCC cells to sunitinib. Combined treatment with lonafarnib overcomes resistance to sunitinib in cell and animal models of human RCC. FT may enhance the antitumor activity of sunitinib, at least in part, through two potential mechanisms: 1) dysregulation of lysosomal sequestration of sunitinib, and 2) suppression of Rheb-dependent mTORC1 activation.

Roles of the Newly Identified Factors in Lysosomal Sequestration of Sunitinib:

The CRISPR/Cas9-based genome-wide screening revealed several cellular factors involved in endosomal/lysosomal formation. To examine the role of these proteins in lysosomal sequestration of sunitinib, individual CRISPR/Cas9-mediated knockouts of RABGGTB, RAB7a, RAB25, RhoB and LAMP2 in 786-O RCC cells can be generated. Based on the analysis of genome-wide screening, knockouts of these target genes may not critical for overall cell viability. Next, 786-O knockout cell sub-lines can be treated with escalating concentrations of sunitinib (LC LABORATORIES®). 786-O cells lacking these genes may be more sensitive to sunitinib than parental 786-O cells. Given that sunitinib shows autofluorescence properties, its total cellular uptake using flow cytometry analysis can be analyzed. Lysosomal accumulation of sunitinib can be examined by co-incubation with Lysotracker Red DND-99 (Life Science Technologies) using fluorescence microscopy. Cell viability and apoptosis can be examined using CELLTITER-BLUE® (PROMEGA®) and TUNEL (Phoenix Flow Systems) assays respectively.

Post-translational prenylation of these proteins (with an exception of LAMP2) is required for their proper endosomal/lysosomal membrane localization and functioning. Therefore, they could represent potential targets for FTIs. To determine the role of post-translational prenylation of the newly identified target proteins in lysosomal sequestration of sunitinib, RAB7a (C205S;C207S), RAB25 (C209S; C210S), and RhoB (C189S;C192S;C193S) proteins with mutated CAAX C-terminal motif can be generated in 786-0 knockout cells lacking the expression of corresponding wild type proteins. The expression of prenylation-deficient proteins may compromise lysosomal sequestration of sunitinib and reinstate its antitumor activity.

Role of the Inhibition of Rheb Farnesylation as a Potential Mechanism Sensitising RCC Cells to Sunitinib:

The effect of treatment with lonafarnib (SELLECK-CHEM®) alone or in combination with sunitinib on mTORC1 activity in RCC cells can be examined. 786-0 and PNX0010 RCC cells can be treated with escalating concentrations of lonafarnib and sunitinib. mTORC1 activity can be evaluated by analyzing the phosphorylation levels of its direct targets S6K and 4EBP1. The farnesylation status of Rheb can be assessed by mobility shift. Because Rheb must be cleaved before farnesylation, farnesylated Rheb migrates faster on SDS-PAGE.

To address the role of Rheb farnesylation in the resistance to sunitinib, CRISPR/Cas9-mediated Rheb knockout in 786-O cells can be carried out. 786-O cells lacking Rheb expression may be more sensitive to sunitinib than parental 786-O cells. Next, farnesylation-independent Rheb mutant Q64L/M184L can be expressed in 786-O Rheb knockout cells. Farnesylation-independent Rheb Q64L/M184L renders tumor cells resistant to FTIs. Therefore, treatment of 786-O cells expressing Rheb Q64L/M184L with lonafarnib may not sensitize the cells to sunitinib-mediated loss of viability and induction of apoptosis. Farnesylation-deficient Rheb C182S mutant can be overexpressed in Rheb knockout 786-O cells. Overexpression of Rheb C182S may reverse sunitinib-resistant phenotype of 786-O cells. Cell viability and apoptosis can be examined as described above. These experiments can be carried out to examine whether lonafarnib enhances the antitumor activity of sunitinib, at least in part, through suppression of Rheb farnesylation. Vectors encoding Rheb mutant constructs are available from Addgene.

Antitumor Efficacy of Combined Treatment with TKs and Lonafarnib Using Patient-Derive RCC Cells:

Established cell lines provide a powerful model to study a tumor's biology. However, it is unlikely that immortal long-term cultured RCC cell lines completely simulate the phenotype of patient-derived RCC cells. Therefore, the antitumor activity of combined treatment with lonafarnib and TKIs can be tested using primary patient-derived RCC cells. Ten tumorigenic patient-derived ccRCC cell cultures have been established. For the proposed experiments, TKIs clinically approved for the treatment of advanced RCC such as sunitinib, pazopanib, sorafenib and axitinib can be used. RCC cells can be treated with escalating concentrations of TKIs with or without lonafarnib. Cell viability and apoptosis can be examined as described herein. The null hypothesis is that treatments with TKIs alone and in combination with lonafarnib produce equal antitumor activity. Alternately, the combined treatment may result in enhanced antitumor activity. The null hypothesis for each tested combination can be rejected if this particular regimen demonstrates superior efficacy in at least 7 out of 8 tested RCC cell lines compared with treatment with a single agent. This test will have 81% power with 3.5% type I error. Statistical justification of these experiments was performed with assistance from Dr. Samuel Litwin, Ph.D. (FCCC Biostatistics).

Statistical Considerations:

Determination of statistically significant differences can be assessed using an independent samples Student's t-test. The nonparametric alternative (Maim-Whitney U) can be used when assumptions for parametric statistical testing have not been met.

Example 3: Evaluation of the Antitumor Efficacy of Combined Sunitinib and Lonafarnib Treatment Using Direct Human-to-Mouse Xenograft Model of ccRCC (Prophetic Example)

Targeted therapies have often given disappointing results when used as single agents in solid tumors. Although TKIs have been combined with other agents in an attempt to improve efficacy and overcome drug resistance, such treatments were often associated with significant toxicities. The data presented herein strongly supports the rationale for combined treatment of RCC with TKIs and FTIs. Specifically, the experiments described herein demonstrate that the concomitant treatment with FTase inhibitor lonafarnib overcomes resistance to sunitinib in cell and animal models of human RCC. Importantly, such treatment is well tolerated by all animals as there are no observed side effects. Furthermore, lonafarnib can be safely combined with various chemotherapeutic agents.

Anti-Tumor Efficacy of Concomitant Treatment with Sunitinib and Lonafarnib in Mouse PDX Models of Human RCC:

PDX is currently the best available approach for the modeling of human malignancies that recapitulate original tumor characteristics. Importantly, orthotopic tumor models accurately predict drug responses in human tumors. Five patient-derived ccRCC models have been established using tissue specimens obtained from patients with highly malignant metastatic ccRCC with enormously short relapse periods after therapeutic courses using sunitinib. Briefly, first passage (F1 tumors) can be generated by subcutaneous implantation of 1-2 mm fragments PDX tumor fragments into the flanks of 6- to 8-week-old C.B17 SCID mice. Second-passage of orthotopic (F2) tumors can be established using F1 tumor fragments. The preliminary experiments document histological resemblance between primary tumors and F1 and F2 xenograft tumors (data not shown). F1 tumor fragments (1-2 mm) can be transplanted under renal capsules of mice. Animals can be monitored for tumor growth by Magnetic Resonance Microscopy (MRM) on a weekly basis. Tumor volumes examined by MRM closely correlate with tumor volumes examined at necropsy (R2>0.9). When tumors reach a mean volume of about 100 mm$^3$, can be randomly assigned to the control or experimental groups. The study design for each gender is as follows:

TABLE 3

| Group | Number of Animals | Agent |
|-------|-------------------|-------|
| 1 | 15 | Vehicle[a] |
| 2 | 15 | Sunitinib |
| 3 | 15 | Lonafarnib |
| 4 | 15 | Sunitinib + Lonafarnib |

[a]10% 2-hydroxypropyl-β-cyclodextrin in PBS. Sunitinib and lonafarnib will be administered at 40 mg/kg five times per week orally. These dose regimens were selected based on the results of our preliminary studies.

Mice can be sacrificed by $CO_2$ inhalation after tumors reach a volume of 1.0 cm$^3$ or before discomfort occurs which may lead to severe pain, distress or death.

Clinical Relevance:

Tumor Size and Evidence of Metastases:

Primary tumors and regional lymph nodes can be resected and measured. Lymph node metastases can be assessed by microscopic examination of H&E-Stained formalin-fixed paraffin-embedded tissues.

Proliferation and Apoptosis:

Proliferation and apoptosis in tumor tissue specimens can be examined using the anti-Ki-67 antibody and ApopTag in situ detection kit (Oncor, Gaithersburg MD) respectively.

Angiogenesis:

Microvessel density can be determined by IHC using anti-mouse-CD31 antibody.

Status of FTase Activity:

Farnesylation status of prelamin-A and HDJ-2 can be assessed by Western blot analysis using anti-Prelamin-A antibody (EMD Millipore) and anti-HDJ-2 antibody (THERMO FISHER SCIENTIFIC®). These proteins are commonly used as markers of effective inhibition of farnesylation. Proteins that have completed farnesylation migrate faster, while non-farnesylated proteins migrate slower, and their ratio reflects FTase inhibition.

Statistical Considerations:

Groups of 15 mice can allow an odds ratio of 5.2 to be distinguished from 1.0 with 80% power and 8% type I error using Fisher's exact test where mice are dichotomized as above or below the grand median tumor volume. Because of the small number of animals, it will not be adjusted for multiple statistical comparisons. The combined treatment with lonafarnib and sunitinib will be considered clinically useful if it yields significant results in at least 50% of target PDX tumors. The null hypothesis that it will yield significant results in at most 5% of PDX tumors versus the 50% alternative can be examined. With 5 different PDX models, the null hypothesis can be rejected if at least 2 of the 5 PDX tumors yield significant results (i.e., p-values at most 0.05). This test has 84% power with 3.0% type I error to distinguish a result applicable to at least 50% of PDX tumors from one applicable to, at most, 5% of them. Survival can be calculated using the Kaplan-Meier method. Differences between groups in tumor volume can be analyzed using the Mann-Whitney U test. Differences in the incidence of metastases between groups can be analyzed using the $\chi^2$ test. Categorical variables can be analyzed using Fisher's exact test.

Various modifications of the described subject matter, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, and the like) cited in the present application is incorporated herein by reference in its entirety.

What is claimed is:

1. A pharmaceutical composition comprising: a tyrosine kinase inhibitor chosen from sunitinib or a pharmaceutically acceptable salt thereof;

lonafarnib, or a pharmaceutically acceptable salt thereof; and a pharmaceutically acceptable carrier, wherein the ratio of the tyrosine kinase inhibitor to lonafarnib is from about 1:1 to about 5:1 (w/w).

2. The pharmaceutical composition according to claim 1, wherein the tyrosine kinase inhibitor is present in an amount from about 1 mg to about 100 mg, from about 5 mg to about 75 mg, from about 10 mg to about 60 mg, or from about 12.5 mg to about 50 mg, and lonafarnib is present in an amount from about 1 mg to about 500 mg, from about 50 mg to about 400 mg, from about 75 mg to about 300 mg, or from about 100 mg to about 200 mg.

3. The pharmaceutical composition according to claim 1, wherein the pharmaceutical composition is an oral dosage form comprising about 12.5 mg, about 25 mg, about 37.5 mg, about 50 mg, about 62.5 mg, about 75 mg, about 87.5 mg, about 100 mg, about 112.5 g, about 125 mg, about 150 mg, about 162.5 mg, about 175 mg, about 197.5 mg, or about 200 mg of lonafarnib.

4. The pharmaceutical composition according to claim 3, wherein the oral dosage form comprises about 25 mg, about 50 mg, about 75 mg, about 100 mg, about 150 mg, or about 200 mg of lonafarnib.

5. The pharmaceutical composition according to claim 1, wherein the tyrosine kinase inhibitor is sunitinib malate.

* * * * *